(12) United States Patent
Kimura

(10) Patent No.: US 8,477,312 B2
(45) Date of Patent: Jul. 2, 2013

(54) TOTAL REFLECTION ILLUMINATED SENSOR CHIP, METHOD FOR PRODUCING THE TOTAL REFLECTION ILLUMINATED SENSOR CHIP, AND SENSING METHOD USING THE TOTAL REFLECTION ILLUMINATED SENSOR CHIP

(75) Inventor: Toshihito Kimura, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 231 days.

(21) Appl. No.: 12/721,303

(22) Filed: Mar. 10, 2010

(65) Prior Publication Data

US 2010/0231915 A1    Sep. 16, 2010

(30) Foreign Application Priority Data

Mar. 11, 2009    (JP) .................................. 2009-057319

(51) Int. Cl.
*G01N 21/55*    (2006.01)

(52) U.S. Cl.
USPC ........................................................ 356/445

(58) Field of Classification Search
USPC ................................................ 356/445–448
See application file for complete search history.

(56) References Cited

U.S. PATENT DOCUMENTS

| | | | |
|---|---|---|---|
| 5,327,225 A | | 7/1994 | Bender et al. |
| 7,395,103 B2 | | 7/2008 | Cappo et al. |
| 8,102,533 B2 | * | 1/2012 | Kimura .......................... 356/445 |
| 2004/0100634 A1 | | 5/2004 | Bartholomew et al. |
| 2006/0066861 A1 | * | 3/2006 | Sato et al. ...................... 356/445 |
| 2006/0119852 A1 | * | 6/2006 | Shimizu ......................... 356/445 |
| 2006/0197954 A1 | * | 9/2006 | Ogura et al. ................... 356/445 |
| 2007/0231924 A1 | * | 10/2007 | Muraishi ....................... 436/518 |

FOREIGN PATENT DOCUMENTS

| | | | |
|---|---|---|---|
| JP | 9-96605 A | | 4/1997 |
| JP | 2003232725 A | * | 8/2003 |

OTHER PUBLICATIONS

Dawson et al. "Imaging of surface plasmon launch and propagation using a photon scanning tunneling microscope", Ultramicroscopy, vol. 57, Nos. 2-3, Feb. 1, 1995, Elsevier, Amsterdam, NL, pp. 287-292, XP022603277.

Lavers, "Determination of the Optical dielectric constants and deformational effects, after surface treatment, of a polymide alignment layer used within a ferroelectric liquid crystal device system", vol. 289, No. 1, Nov. 30, 1996, pp. 133-139, XP004055556.

Sterligov et al., "Elastic scattering of surface electromagnetic waves by ID surface relief", Optics Communications, vol. 177, Nos. 1-6, Apr. 1, 2000, North-Holland Publishing Co., Amsterdam, NL., pp. 1-8, XP004195372.

* cited by examiner

*Primary Examiner* — Hoa Pham
(74) *Attorney, Agent, or Firm* — Birch, Stewart, Kolasch & Birch, LLP

(57) ABSTRACT

A total reflection illuminated sensor chip is employed in a detecting method for detecting a detection target substance including the steps of: supplying a sample that includes the detection target substance onto a metal film formed on a surface of a dielectric prism, irradiating a measuring light beam onto the interface between the dielectric prism and the metal film such that conditions for total reflection are satisfied at the interface, and utilizing evanescent waves which are generated due to the irradiation of the measuring light beam to detect the detection target substance. Polishing streaks in the region of a metal film formation surface of the dielectric film, on which the metal film is formed, have directional properties with respect to a single direction.

6 Claims, 14 Drawing Sheets

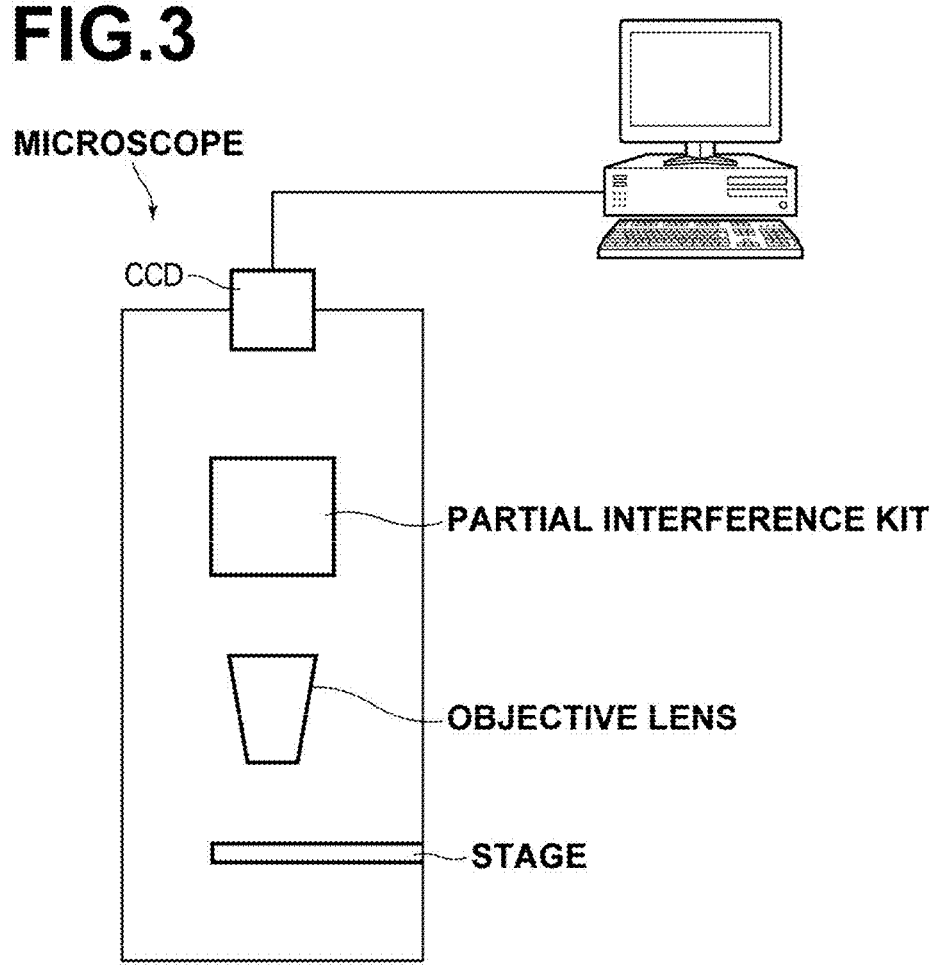

Image-A

Image-B

Image-C

FFT-A

FFT-B

FFT-C

FFT-A 0.39um/cycle

100um/cycle

FIG.9 MEASURING LIGHT BEAM LEAKING THROUGH POLISHING STREAKS
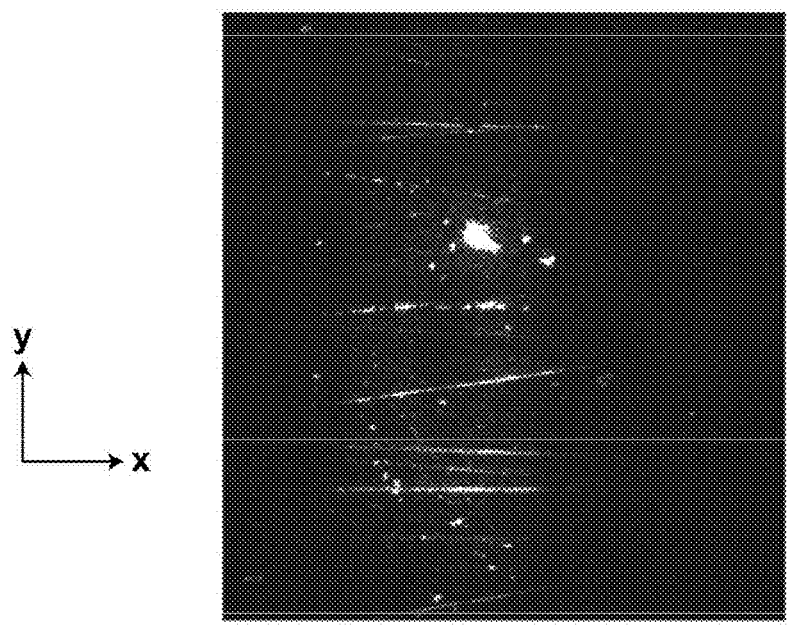
FIG.10
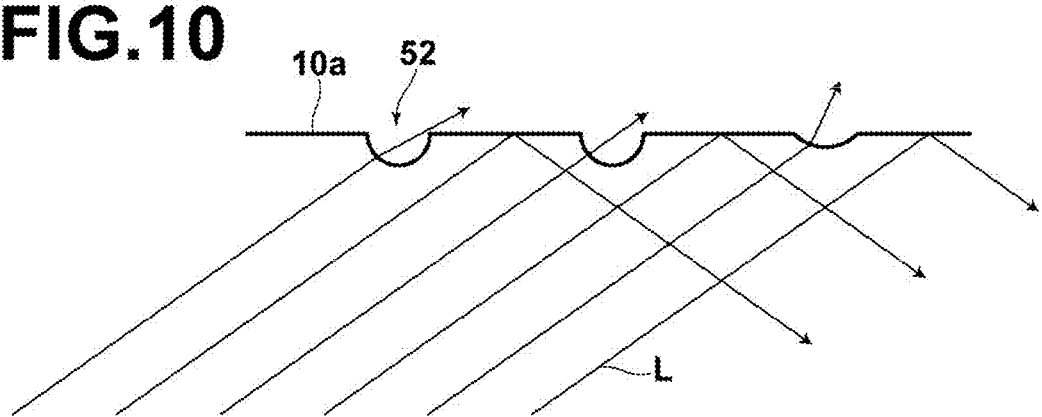

TOTAL REFLECTION ILLUMINATED SENSOR CHIP, METHOD FOR PRODUCING THE TOTAL REFLECTION ILLUMINATED SENSOR CHIP, AND SENSING METHOD USING THE TOTAL REFLECTION ILLUMINATED SENSOR CHIP

BACKGROUND OF THE INVENTION

1. Field of the Invention

The present invention is related to a total reflection illuminated sensor chip, which is employed in a method for detecting substances within samples by utilizing evanescent waves.

2. Description of the Related Art

Conventionally, detecting methods that utilize evanescent waves or surface plasmon induced by totally reflected illumination are being focused on, in biological measurements for detecting proteins, DNA, and the like. Surface plasmon are compression waves of free electrons which are generated by the free electrons vibrating as a group at the surfaces of metals. SPFS (Surface Plasmon Field enhanced fluorescence Spectroscopy) measurement is an example of a detecting method that utilizes the electric field enhancing effect of surface plasmon.

SPFS measurement is a method in which detection target substances are detected, by: generating evanescent waves on a metal film that functions as a detecting portion provided on a dielectric prism; exciting the detection target substances included in samples or fluorescent labels attached to the detection target substances by the evanescent waves; and detecting the fluorescence emitted by the detection target substance or the fluorescent labels. The evanescent waves are generated on the metal film, by causing a measuring light beam to be totally reflected at the interface between the dielectric prism and the metal film provided thereon. SPFS measurement is easy to execute, and is capable of measuring a plurality of samples simultaneously. Further, the electric field enhancing effect of surface plasmon, which is generated by the evanescent waves resonating with free electrons in the metal film, amplify the evanescent waves, and enables great fluorescent signals to be detected. Accordingly, SPFS measurement is widely used.

In the aforementioned SPFS measurement, measuring light beams are totally reflected at interfaces between dielectric prisms and a detecting portion. Therefore, dielectric prisms, on predetermined regions of which detecting portions are formed, are commonly employed as sensor chips (refer to Japanese Unexamined Patent Publication No. 9 (1997)-096605). Presently, dielectric prisms formed of plastic, which are less expensive and more easily molded than glass, are commonly employed.

The detection limits of SPFS measurement are determined by: (i) background light (leakage of light within a measuring apparatus); (ii) scattering of a measuring light beam; (iii) autofluorescence of an optical system due to the scattering of the measuring light beam; and (iv) background light formed by autofluorescence of a sensor chip, and not from fluorescent labels. The influence of (i) can be comparatively easily reduced by design of the apparatus. The influence of (ii) can also be easily reduced by providing a measuring light beam cutoff filter. The influence of (iv) is comparatively small, because excitation is performed via a metal film on the sensor chip.

However, in cases that the intended use of sensor chips is laboratory testing, it is not possible to expend much cost on the sensor chips. In this case, it is difficult to stably produce sensor chips that do not have burrs and ridged structures (polishing streaks) formed during the molding process. Therefore, it is difficult to avoid the influence of (iii) above. This is because portions of measuring light beams leak through polishing streaks on surfaces on which metal films are formed (metal film formation surfaces), resulting in increased noise.

In homogenous assay systems that take advantage of the characteristic of SPFS measurement, that only signals in the vicinity of a metal film are strongly excited, and perform fluorescence detection without performing cleansing to detect the amount of a detection target substance from the variance (rate) of fluorescent signals, another factor: (v) influence of fluorescence from floating labels due to scattering of a measuring light beam; is added, and becomes a grave problem.

SUMMARY OF THE INVENTION

The present invention has been developed in view of the foregoing circumstances. It is an object of the present invention to provide a total reflection illuminated sensor chip capable of preventing leakage of light due to polishing streaks, caused by polishing a metal film formation surface, during detection of bioactive substances that utilizes evanescent waves, to enable highly quantitative detection. It is another object of the present invention to provide a method for producing the total reflection illuminated sensor chip. It is still another object of the present invention to provide a sensing method that employs the total reflection illuminated sensor chip.

A total reflection illuminated sensor chip of the present invention that achieves the above object is a total reflection illuminated sensor chip, which is employed in a detecting method for detecting a detection target substance comprising the steps of: supplying a sample that includes the detection target substance onto a metal film formed on a surface of a dielectric prism, irradiating a measuring light beam onto the interface between the dielectric prism and the metal film such that conditions for total reflection are satisfied at the interface, and utilizing evanescent waves which are generated due to the irradiation of the measuring light beam to detect the detection target substance, the total reflection illuminated sensor chip comprising:

the dielectric prism; and the metal film; characterized by:

polishing streaks in the region of a metal film formation surface of the dielectric film, on which the metal film is formed, having directional properties with respect to a single direction.

Here, the expression "detecting a detection target substance" refers not only to detecting the qualitative amounts, that is, whether the detection target substance is present, but also to detecting quantitative amounts of the detection target substance, and detecting the degree of activity thereof.

The term "metal film formation surface" refers to a surface of the dielectric prism, on which the metal film is formed.

The term "polishing streaks" refers to streaked burrs or streaked structures, which are formed on the metal film formation surface of the dielectric prism, due to polishing. That is, the polishing streaks include not only streaked burrs which are formed by the metal film formation surface being polished directly, but also streaked structures which are transferred from a molding die in the case that polishing streaks are formed on the molding die by polishing. Generally, the former polishing streaks are continuous elongate grooves, whereas the latter polishing streaks are continuous elongate ridges.

The expression "having directional properties with respect to a single direction" refers to a state in which the polishing streaks are substantially formed along a single direction. That is, the expression refers not only to cases in which a plurality of polishing streaks extend along a single direction perfectly parallel to each other, but also includes cases in which a plurality of polishing streaks intersect with each other, while being formed along a single direction as a whole to a degree that enables obtainment of practical operational effects. More specifically, the expression "having directional properties" as used in the present specification refers to cases in which the absolute value of the degree of the directional properties of the polishing streaks is 3% or greater, as calculated by a spatial frequency analysis method which will be described in detail in the embodiments.

Further, it is preferable for the total reflection illuminated sensor chip of the present invention to adopt a configuration, wherein:

the dielectric prism has a light transmitting surface, through which the measuring light beam is transmitted; and the light transmitting surface is formed such that projection vectors that represent components of the normal vector of the light transmitting surface, which are projected onto the metal film formation surface, are substantially parallel to directional vectors that represent the directional properties of the polishing streaks.

Here, the term "projection vectors" refer to vectors that represent components which are projected onto the metal film formation surface. In addition, the normal vector of the light transmitting surface may be designated as desired.

The "directional vectors" that represent the directional properties of the polishing streaks are calculated by a spatial frequency analysis method from the density in the vicinity of a kx axis and the density in the vicinity of a ky axis within FFT (Fast Fourier Transform) processed images of images of the polishing streaks, as will be described in detail in the embodiments. The directional vectors are vectors that represent the directions and degrees of the directional properties.

The "spatial frequency analysis method" is a method for calculating the degree of the directional properties of the polishing streaks, from the density in the vicinity of a kx axis and the density in the vicinity of a ky axis within FFT processed images of images of the polishing streaks. The details of the calculating method will be described in detail in the embodiments.

The expression "substantially parallel" refers not only to cases in which the vectors are completely parallel, but also to cases in which the vectors are shifted from parallel states to a degree that still enables obtainment of practical operational effects.

It is preferable for projection vectors that represent components of the measuring light beam, which are projected onto the metal film formation surface, to be substantially parallel to directional vectors that represent the directional properties of the polishing streaks. Alternatively, it is preferable for the propagation direction of the evanescent waves and the surface plasmon, which are generated by resonance of the metal film, to be substantially parallel to the direction in which the polishing streaks exhibit directional properties.

Here, the term "measuring light beam" refers to light that enters the interface between the dielectric prism and the metal film.

Further, it is preferable for the degree of the directional properties of the polishing streaks to be +10% or greater, as calculated by the spatial frequency analysis method.

It is preferable for the dielectric prism to be formed by a synthetic resin material. Here, the expression "formed by a synthetic resin material" refers to cases in which synthetic resin materials are the main component of the dielectric prism. A component which is included at 90% by weight or greater is referred to as a "main component".

A first method for producing the total reflection illuminated sensor chip of the present invention is a method for producing a total reflection illuminated sensor chip equipped with a dielectric prism and a metal film formed on a surface of the dielectric prism, which is employed in a detecting method for detecting a detection target substance comprising the steps of: supplying a sample that includes the detection target substance onto the metal film, irradiating a measuring light beam onto the interface between the dielectric prism and the metal film such that conditions for total reflection are satisfied at the interface, and utilizing evanescent waves which are generated due to the irradiation of the measuring light beam to detect the detection target substance, comprising the steps of:

molding the dielectric prism; and polishing a metal film formation surface, which is the surface on which the metal film is formed, such that polishing streaks formed thereby have directional properties with respect to a single direction.

Here, the expression "molding" refers to molding in which materials are placed in dies, as well as photolithography and the like, in which materials are not placed in dies.

It is preferable for the first method for producing the total reflection illuminated sensor chip of the present invention to further comprise the step of:

forming a light transmitting surface, through which the measuring light beam is transmitted. In this case, the metal film formation surface is polished such that projection vectors that represent components of the normal vector of the light transmitting surface, which are projected onto the metal film formation surface, are substantially parallel to directional vectors that represent the directional properties of the polishing streaks.

It is preferable for the metal film formation surface to be polished such that the degree of the directional properties of the polishing streaks is +10% or greater, as calculated by a spatial frequency analysis method. It is also preferable for synthetic resin to be employed as the material of the dielectric prism.

A second method for producing the total reflection illuminated sensor chip of the present invention is a method for producing a total reflection illuminated sensor chip equipped with a dielectric prism and a metal film formed on a surface of the dielectric prism, which is employed in a detecting method for detecting a detection target substance comprising the steps of: supplying a sample that includes the detection target substance onto the metal film, irradiating a measuring light beam onto the interface between the dielectric prism and the metal film such that conditions for total reflection are satisfied at the interface, and utilizing evanescent waves which are generated due to the irradiation of the measuring light beam to detect the detection target substance, comprising the steps of:

polishing a portion of a die for molding the dielectric prism that corresponds to a metal film formation surface, on which the metal film is formed, such that polishing streaks have directional properties with respect to a single direction; and using the die to mold the dielectric prism.

Here, the expression "portion of a die for molding the dielectric prism that corresponds to a metal film formation surface" refers to the portion of the die for molding the dielectric prism at which the metal film formation surface is molded. That is, the "portion of a die . . . that corresponds to a metal film formation surface" refers to a portion of the interior of the die that contacts the metal film formation surface.

It is preferable for the second method for forming the total reflection illuminated sensor chip of the present invention to further comprise the step of:

forming a light transmitting surface, through which the measuring light beam is transmitted such that projection vectors that represent components of the normal vector of the light transmitting surface, which are projected onto the metal film formation surface, are substantially parallel to directional vectors that represent the directional properties of the polishing streaks.

In addition, it is preferable for the portion of the die that corresponds to the metal film formation surface to be polished such that the degree of the directional properties of the polishing streaks is +10% or greater, as calculated by a spatial frequency analysis method.

A sensing method of the present invention is a sensing method for detecting a detection target substance, comprising the steps of:

supplying a sample that includes the detection target substance onto a metal film formed on a surface of a dielectric prism;

irradiating a measuring light beam onto the interface between the dielectric prism and the metal film such that conditions for total reflection are satisfied at the interface; and utilizing evanescent waves which are generated due to the irradiation of the measuring light beam to detect the detection target substance;

polishing streaks in the region of a metal film formation surface of the dielectric film, on which the metal film is formed, having directional properties with respect to a single direction; and the measuring light beam being irradiated onto the interface such that projection vectors that represent components of the measuring light beam, which are projected onto the metal film formation surface, are substantially parallel to directional vectors that represent the directional properties of the polishing streaks.

The total reflection illuminated sensor chip of the present invention and the method for producing the total reflection illuminated sensor chip of the present invention are characterized by the directions of the projected components of the measuring light beam with respect to the metal film formation surface and the direction of the directional properties of the polishing streaks on the metal film formation surface being substantially parallel. Thereby, regions at the interface between the dielectric prism and the metal film, at which the measuring light beam does not satisfy the conditions for total reflection are reduced, resulting in a decrease in the amount of the measuring light beam that leaks through the polishing streaks. Accordingly, autofluorescence of an optical system due to the scattering of the measuring light beam and the influence of fluorescence from floating labels due to scattering of the measuring light beam can be reduced, and more highly quantitative detection becomes possible.

BRIEF DESCRIPTION OF THE DRAWINGS

FIG. 3 is a diagram that illustrates the schematic construction of an apparatus for obtaining differential interference images of polishing streaks.

FIG. 9 is a diagram that illustrates a state in which a measuring light beam is leaking through polishing streaks.

FIG. 10 is a diagram for explaining a state in which polishing streaks preclude conditions for total reflection from being satisfied.

DESCRIPTION OF THE PREFERRED EMBODIMENTS

Hereinafter, embodiments of the present invention will be described with reference to the attached drawings. However, the present invention is not limited to the embodiments to be described below.

Total Reflection Illuminated Sensor Chip and Production Method

<First Embodiment>

Figure 1A:
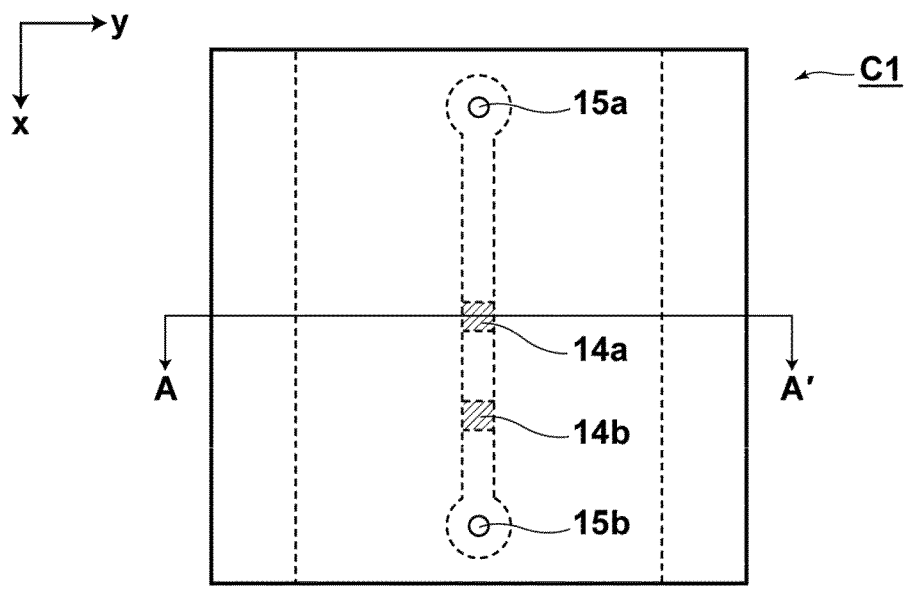
FIG. 1A is a plan view that illustrates the schematic structure of a total reflection illuminated sensor chip according to a first embodiment of the present invention.
Figure 1B:
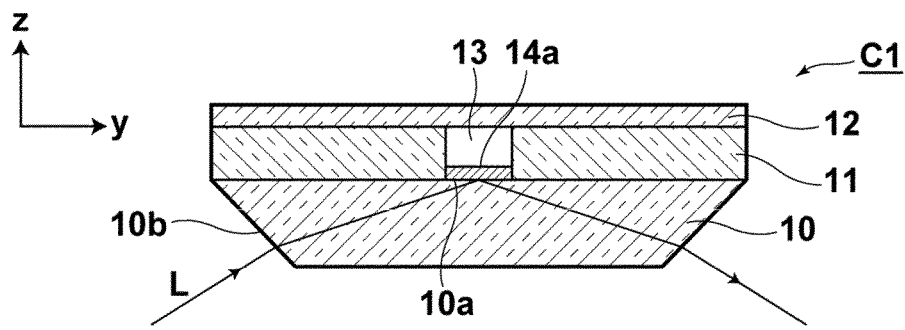
FIG. 1B is a sectional view that illustrates the schematic structure of the total reflection illuminated sensor chip according to the first embodiment of the present invention.

First, the construction of a total reflection illuminated sensor chip C1 according to a first embodiment of the present invention will be described. FIGS. 1A and 1B are a plan view and a sectional view that illustrates the schematic structure of the total reflection illuminated sensor chip C1 of the first embodiment, respectively. Here, FIG. 1B is a sectional view taken along line A-A' of FIG. 1A. Note that in order to facilitate visual recognition, the dimensions of the components within the drawings are not the actual dimensions thereof.

As illustrated in FIGS. 1A and 1B, the total reflection illuminated sensor chip C1 is equipped with: a dielectric prism 10; side wall materials 11 that function as side walls of a flow channel 13 which is formed on the dielectric prism 10; a lid member 12 that functions as the top surface of the flow channel 13; and metal films 14a and 14b, which are formed at predetermined regions within the flow channel 13.

The dielectric prism 10 functions as a substrate, on which the flow channel 13, through which samples that include detection target substances and the like are caused to flow, is formed. In addition, the dielectric prism 10 is also equipped with a first light transmitting surface 10b (a surface of the dielectric prism through which a measuring light beam enters the dielectric prism), through which a measuring light beam enters when propagating toward an interface between the dielectric prism 10 and the metal films 14a and 14b. Note that it is not necessary for the light transmitting surface 10b to be inclined with respect to a z-y plane. In addition, the light transmitting surface 10b is not strictly necessary. In the coordinate system employed in FIG. 1A, the downward direction is designated as the x axis, the rightward direction is designated as the y axis, and the direction perpendicular to the drawing sheet is designated as the z axis, to form a right hand coordinate system. That is, the direction of projected components of a measuring light beam L with respect to a metal film formation surface 10a (the surface of the dielectric prism on which the metal films are formed) is the y axis, the direction perpendicular to and extending above the metal film formation surface 10a is the z axis, and the x axis is designated to form a right hand coordinate system (in the present specification, the coordinate system which is employed will be this right hand coordinate system, unless otherwise noted). In addition, it is preferable for the light transmitting surface 10b to be formed such that projection vectors that represent components of the normal vector of the light transmitting surface 10b, which are projected onto the metal film formation surface 10a, are substantially parallel to the y axis (directional vectors that represent the directional properties of the polishing streaks, to be described later). The material of the dielectric prism 10 is a transparent material, such as a transparent resin or glass. It is desirable for the dielectric prism 10 to be formed by a synthetic resin (plastic) material. In the case that the dielectric prism 10 is formed by resin, polymethyl methacrylate (PMMA), polycarbonate (PC), non crystalline polyolefin (APO) that includes cycloolefin, and ZEONEX (by Japan Zeon Co.) may be favorably employed. The metal film formation surface 10a is polished such that polishing streaks are formed along the y axis.

The flow channel 13 is formed by the side wall materials 11 formed on the dielectric prism 10, and the lid member 12 which is fitted on the side wall materials 11. Further, liquid reservoirs for injecting liquids or discharging liquids are formed at the ends of the flow channel 13. In addition, the metal films 14a and 14b that function as detecting portions are formed at predetermined regions within the flow channel 13. In the first embodiment, the metal film 14a is employed as a measurement detecting portion, and the metal film 14b is employed as a reference detecting portion. However, the reference detecting portion is not necessary, as long as one measurement detecting portion is provided. The material of the metal films 14a and 14b is not particularly limited. Examples of materials which are desirable from the viewpoint of inducing plasmon include Au, Ag, Cu, Pt, Ni, and Ti. Among these, Au and Ag, which exhibit high electric field enhancing effects, are particularly preferred. It is desirable for the thicknesses of the metal films 14a and 14b to be determined such that surface plasmon is strongly excited, taking the material of the metal films 14a and 14b and the wavelength of the measuring light beam L into consideration. For example, in the case that a laser beam having a central wavelength of 780 nm is employed as the measuring light beam L, and Au is employed as the material of the metal films 14a and 14b, a favorable thickness of the metal films 14a and 14b is 50 nm±5 nm. The metal films may be provided on the dielectric prism 10 by forming a mask having openings at the predetermined regions, then employing a known sputtering method, a vapor deposition method, or the like.

The side wall materials 11 form the side walls of the flow channel 13 by being provided on the dielectric prism 10 with a gap therebetween. The side wall materials 11 may be adhesively attached as sealing members, to form the flow channel 13. The side wall materials 11 are provided to form a space which is wider than the width of the flow channel 13, in order to secure space for the liquid reservoirs for injecting liquids or discharging liquids are formed at the ends of the flow channel 13. The lid member 12 forms the top surface of the flow channel 13, by being fitted on the side wall materials 11. An injection opening 15a, which is connected to the liquid reservoir for injecting liquids and functions to inject fluids therein, and an air aperture 15b, which is connected to the liquid reservoir for discharging liquids and functions to suction air therefrom, are formed in the lid member 12. The same materials listed previously as materials for the dielectric prism 10 may be employed as the material of side wall materials 11 and the lid member 12. Alternatively, a glass gapped cover or a molded article, in which the side wall materials 11 and the lid member 12 are formed integrally, may be employed.

Figure 2A:
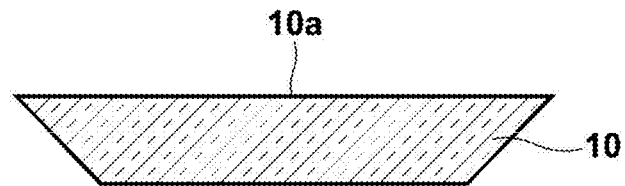
FIGS. 2A through 2E are collection of diagrams that illustrates a method for producing the total reflection illuminated sensor chip according to the first embodiment of the present invention.
Figure 2B:
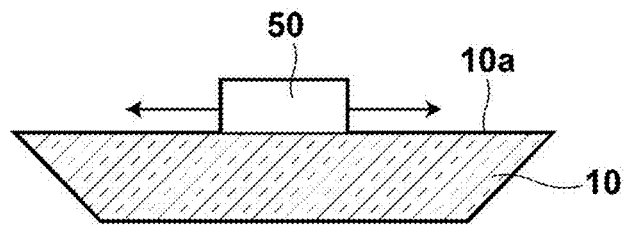
Figure 2C:
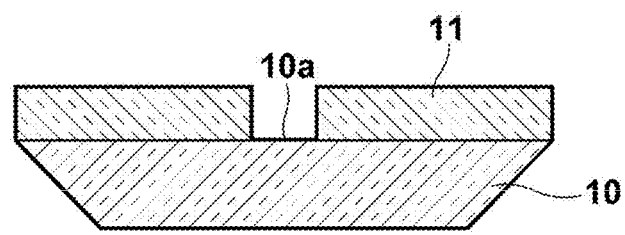
Figure 2D:
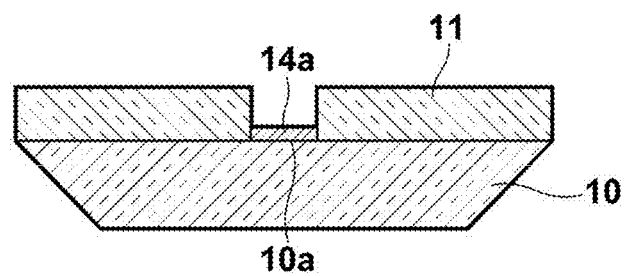
Figure 2E:
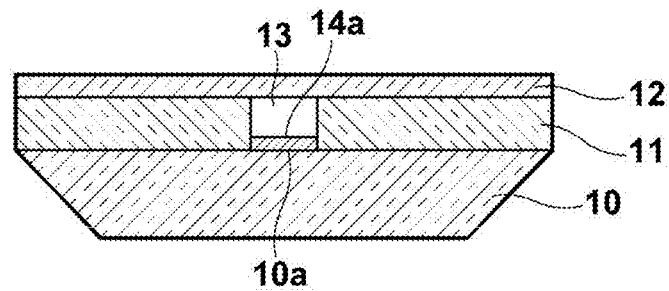

Next, a method for producing the total reflection illuminated sensor chip C1 will be described with reference to FIGS. 2A through 2E. First, the dielectric prism 10, which functions as the substrate of the sensor chip, is formed by molding (FIG. 2A). Then, the metal film formation surface 10a of the dielectric prism 10 is polished with a polishing material 50 in the directions indicated by the arrows in FIG. 2B, such that polishing streaks are formed along the y axis (FIG. 2B). Next, the side wall materials 11 are provided on the metal film formation surface 10a to form the side walls of the flow channel 13 (FIG. 2C). Thereafter, the metal films 14a and 14b are formed at predetermined regions within the flow channel (FIG. 2D). Finally, the lid member 12 is fitted on the side wall materials 11 (FIG. 2E).

The molding of the dielectric prism 10 is not particularly limited. The dielectric prism 10 may be produced by injection molding, photolithography, or by other common methods. Alternatively, commercially available dielectric prisms may be utilized.

The polishing of the metal film formation surface 10a is performed such that the polishing streaks are formed along the y axis, that is, such that the polishing streaks have directional properties with respect to the direction of the y axis. The polishing may be performed initially in a circular manner such that the entirety of the metal film formation surface 10a is uniformly polished, and then polishing may be performed along the y axis, as long as the polishing streaks ultimately have directional properties with respect to the direction of the y axis. Here, the polishing material 50 is not particularly limited. Examples of the polishing material 50 which may be employed for manual polishing include: Resin Polishing Agent 24P by Yanase K.K.; DANDEE D-491 by K.K. Koyo, Inc. Alternatively, SUNLIGHT KFF-W by K.K. Koyo, Inc. may be mounted to a polisher to perform polishing.

The directional properties of the polishing streaks are defined in numerical terms by the spatial frequency analysis method described below.

Figure 4A:
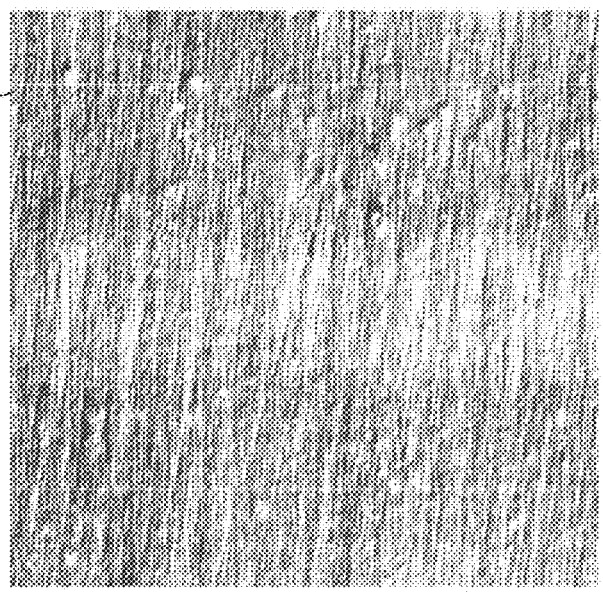
FIG. 4A is a diagram that illustrates a differential interference image of polishing streaks which are formed to extend along a y axis.
Figure 4B:
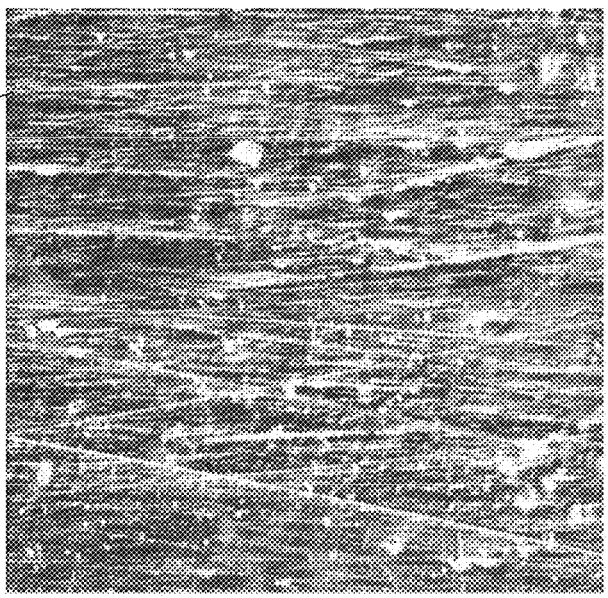
FIG. 4B is a diagram that illustrates a differential interference image of polishing streaks which are formed to extend along an x axis.
Figure 4C:
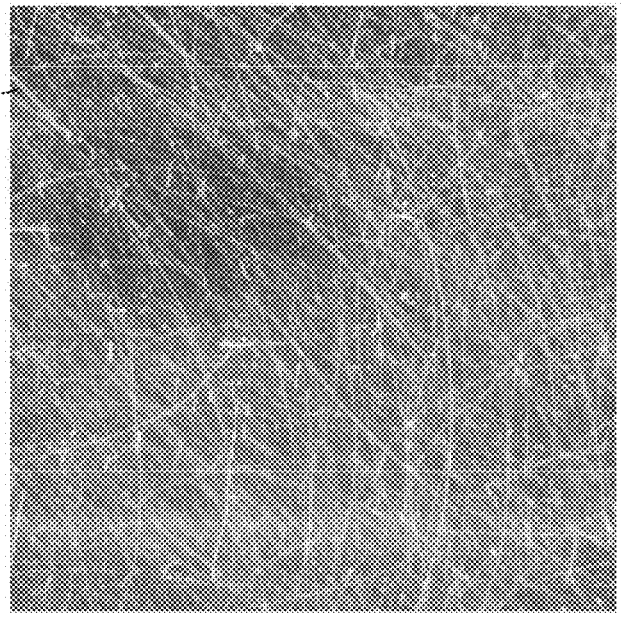
FIG. 4C is a diagram that illustrates a differential interference image of polishing streaks which are formed by performing polishing in a circular manner.

(1) Differential images of the polishing streaks on the metal film formation surface are obtained. FIG. 3 is a diagram that illustrates the schematic construction of an apparatus for obtaining differential interference images (hereinafter, simply referred to as "images") of polishing streaks. Here, BX51WI by Olympus K.K. is employed as a microscope, LMPlanFIx50 by Olympus K.K. is employed as an objective lens. And ADT-100 by K. K. Flovel is employed as a CCD. A personal computer for storing and processing images is connected to the CCD. When the above apparatus is employed to obtain images of the polishing streaks, images such as those illustrated in FIGS. 4A through 4C are obtained. Image-A of FIG. 4A is an image of a dielectric prism, which has been polished such that polishing streaks are formed along the y axis. Image-B of FIG. 4B is an image of a dielectric prism, which has been polished such that polishing streaks are formed along the x axis. Image-C of FIG. 4C is an image of a dielectric prism, which has been polished in a circular manner.

Figure 5:
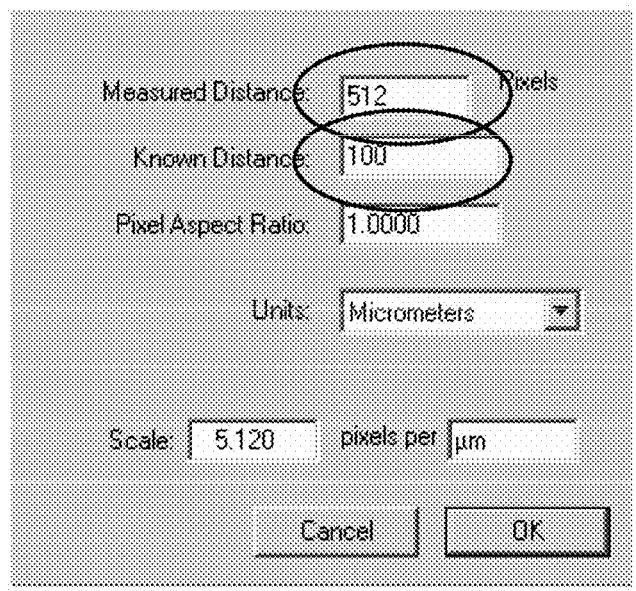
FIG. 5 is a diagram that illustrates a setting screen of image processing software which is utilized in the first embodiment.
Figure 6A:
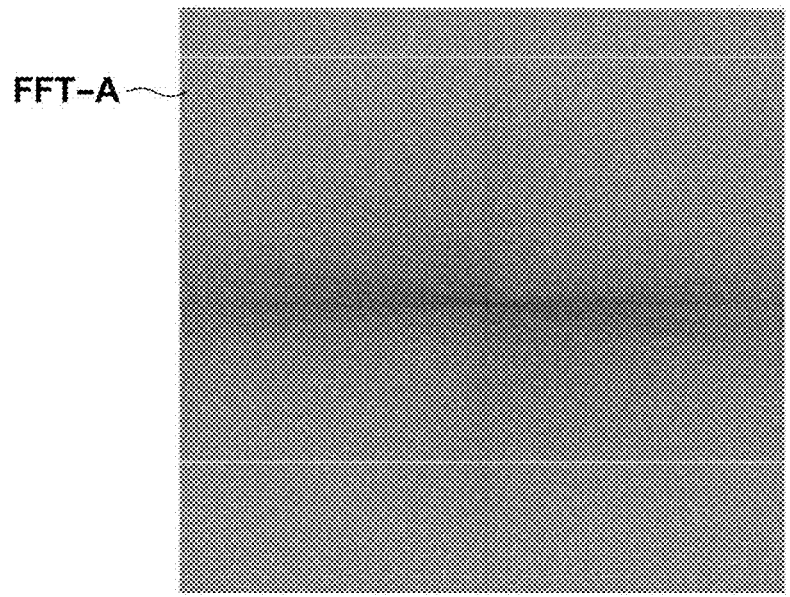
FIG. 6A is a diagram that illustrates an FFT image of a differential interference image of polishing streaks which are formed to extend along a y axis.
Figure 6B:
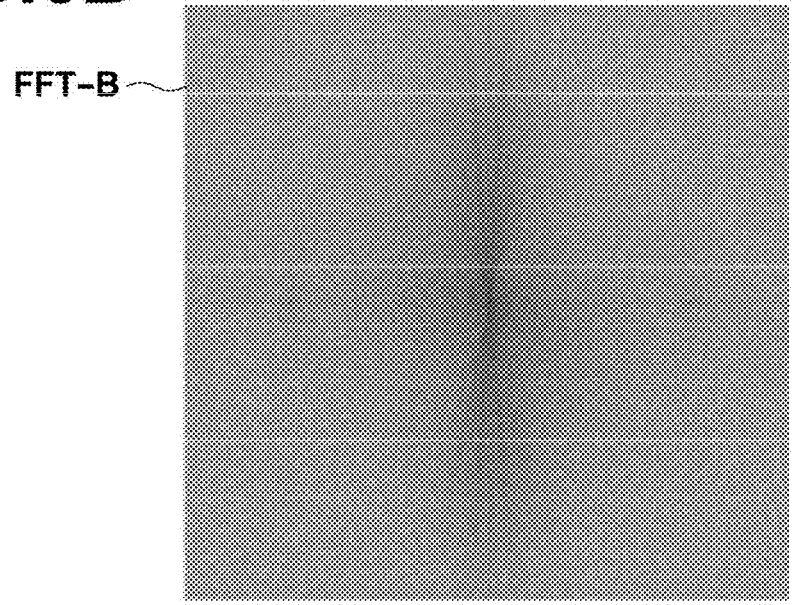
FIG. 6B is a diagram that illustrates an FFT image of a differential interference image of polishing streaks which are formed to extend along an x axis.
Figure 6C:
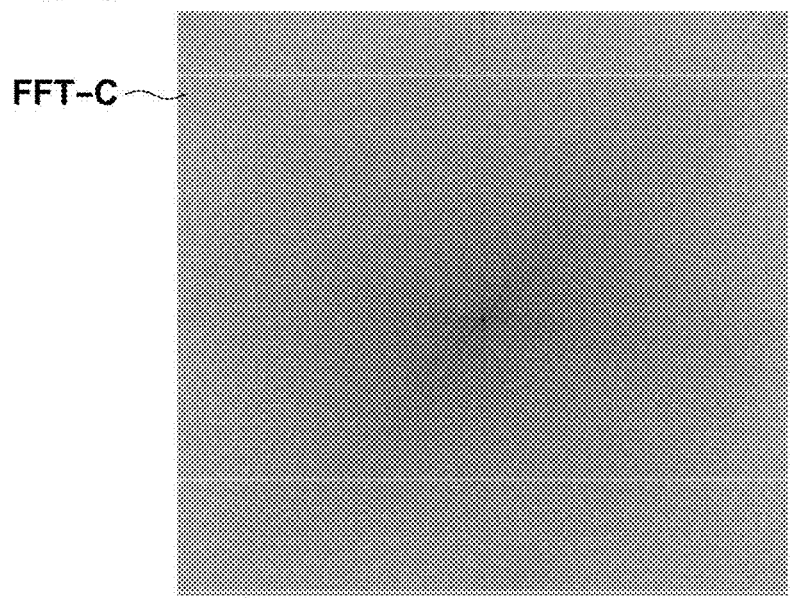
FIG. 6C a diagram that illustrates an FFT image of a differential interference image of polishing streaks which are formed by performing polishing in a circular manner.
Figure 7:
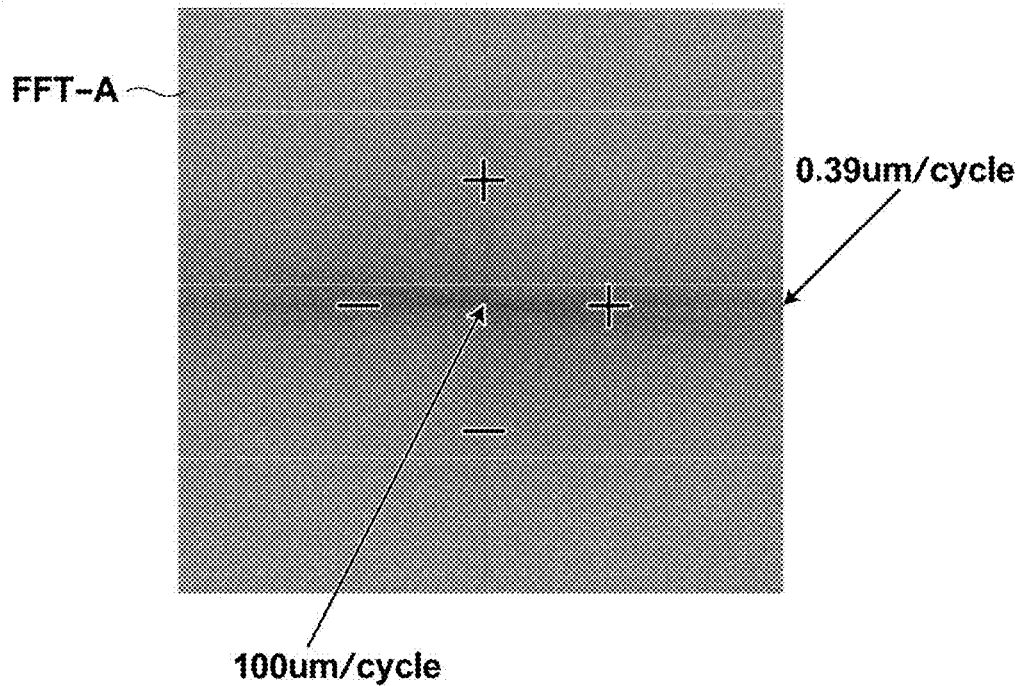
FIG. 7 is a diagram for explaining low frequency components and high frequency components within an FFT image.

(2) Fast Fourier Transform is administered onto the images of the polishing streaks. Next, an FFT (Fast Fourier Transform) process is administered to each of the images obtained in (1), to obtain FFT images of the polishing streaks. The FFT process is performed employing image processing software Scion Image. Here, it is necessary to set the units of measurement to actual dimensions in a setting screen of Scion Image. For example, FIG. 5 illustrates a case in which the images obtained in (1) are 512×512 pixels and represent a 100 µm field of view. When the FFT process is administered on the images, FFT images such as those illustrated in FIGS. 6A through 6C are obtained. FFT-A, FFT-B, and FFT-C are FFT images corresponding to Image-A, Image-B, and Image-C, respectively. FFT images are images that represent the powers (squares of absolute values) of frequency components within original images as densities. The powers of low frequency components are represented toward the centers of FFT images, while the powers of high frequency components are represented at positions within the FFT images away from the centers thereof (refer to FIG. 7).

Figure 8:
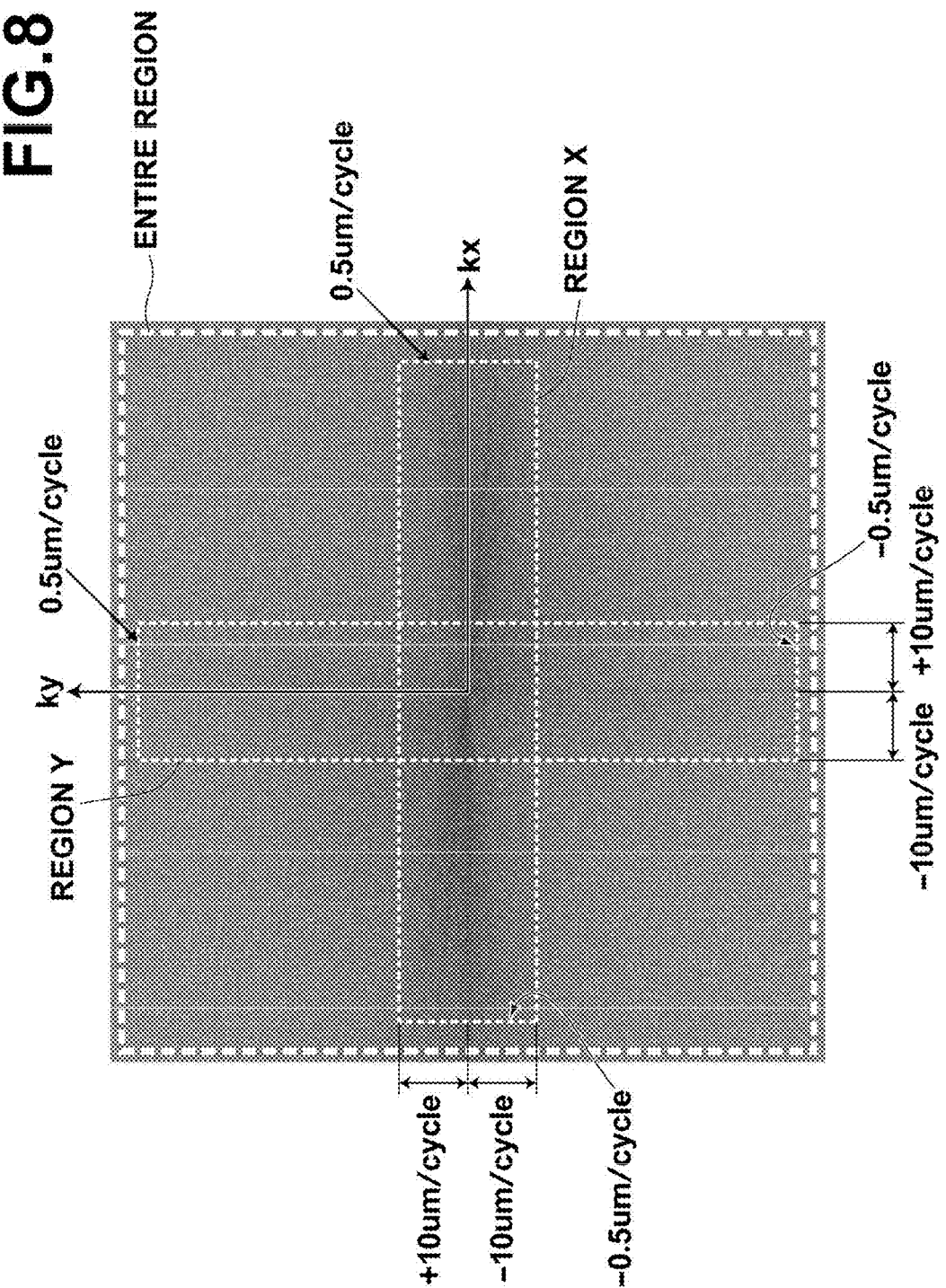
FIG. 8 is a diagram for explaining extraction of regions from within an FFT image during quantification of directional properties.

(3) The density in a region near a kx axis and the density in a region near a ky axis within the FFT images are quantified, and the degree of directional properties of the polishing streaks are calculated. For example, the density in the vicinity of a kx axis within an FFT image suggests that periodic structures are present in the direction of the x axis within an original image. Similarly, the density in the vicinity of a ky axis within an FFT image suggests that periodic structures are present in the direction of the y axis within an original image. That is, an FFT image illustrates that structures that extend along the y axis of an original image are present in the case that the density concentration in the vicinity of the kx axis of the FFT image is high. Similarly, an FFT image illustrates that structures that extend along the x axis of an original image are present in the case that the density concentration in the vicinity of the ky axis of the FFT image is high. Here, the kx axis and the ky axis represent spatial frequency coordinates within the FFT images. As illustrated in FIG. 8, the rightward and upward directions within the FFT images are designated as the kx axis and the ky axis, respectively. In the present invention, The density in a region near the kx axis and the density in a region near the ky axis within the FFT images are extracted and defined in numerical terms. Then, the degrees of directional properties of the polishing streaks are defined from the densities, which have been defined in numerical terms. Here, the region near the kx axis refers to a region in which the values of the kx axis are 0.5 µm/cycle or greater and the values in the ky axis direction are 10 µm/cycle or greater (region X within FIG. 8), and the region near the ky axis refers to a region in which the values of the ky axis are 0.5 µm/cycle or greater and the values in the kx axis direction are 10 µm/cycle or greater. The reason why the region is designated as that representing lower frequency components than 0.5 µm/cycle is based on empirical data that indicates that light leaks through polishing streaks having widths of 0.5 µm or greater. The FFT images are symmetric at the centers thereof (refer to FIG. 7). Therefore, only the positive sides of each axis may be quantified. However, in the present specification, a description will be given for a case in which both the positive and negative sides of each axis are quantified.

The degree of directional properties of the polishing streaks in actual space is defined as follows.

Degree of Directional Properties(%)=(Density of Region X(%))−(Density of Region Y(%))

Here, the density of region X (%) refers to (average density of region X−average density of entire image)/(average density of entire image)×100. The density of region Y (%) refers to (average density of region Y−average density of entire image)/(average density of entire image)×100. In addition, the "entire image" refers to the entirety of the FFT image, but is not limited to this definition, and may refer to a region which is specified to be large enough to include both region X and region Y. The average density within each region may be quantified by a function of the image processing software Scion Image. If numerical values that represent the degrees of directional properties of the polishing streaks are positive, this indicates that there are more structures formed along the y axis than along the x axis in actual space, that is, that the polishing streaks have directional properties in the direction of the y axis. Conversely, if numerical values that represent the degrees of directional properties of the polishing streaks are negative, this indicates that there are more structures formed along the x axis than along the y axis in actual space, that is, that the polishing streaks have directional properties in the direction of the x axis.

When the spatial frequency analysis method was applied to the three FFT images illustrated in FIGS. 6A through 6C to quantify the degrees of directional properties thereof, the results were those illustrated in Table 1 below.

TABLE 1

|       | Average Density of Region X | Average Density of Region Y | Average Density of Entire Region | Density of Region X (%) ① | Density of Region Y (%) ② | Degree of Directional Properties (%) ①-② |
|-------|---|---|---|---|---|---|
| FFT-A | 137.6 | 121.6 | 116.9 | 17.7 | 4.0 | 13.7 |
| FFT-B | 109.8 | 118.7 | 102.8 | 6.8 | 15.5 | −8.7 |
| FFT-C | 117 | 115.7 | 104.6 | 11.9 | 10.6 | 1.3 |

FFT-A is an FFT image corresponding to Image-A of FIG. 4A. Therefore, the directional properties of the polishing streaks with respect to the direction of the y axis is high, at 13.7%. FFT-B is an FFT image corresponding to Image-B of FIG. 4B. Therefore, the directional properties of the polishing streaks with respect to the direction of the x axis is high, at 8.7%. FFT-C is an FFT image corresponding to Image-C of FIG. 4C, illustrating a case in which polishing is performed in a circular manner. Therefore, the directional properties thereof are low. From the viewpoint of measurement sensitivity, it is preferable for the degree of directional properties to be +5% or greater, and more preferably +10% or greater. Here, vectors that represent the magnitude of the degree and the orientation of the directional properties are referred to as directional vectors. That is, a vector in the y axis direction having a value of 10 corresponds to a degree of directional properties of +10%.

The operation of the sensor chip of the present invention will be described. The present applicants discovered a phenomenon that measuring light beams leak through polishing streaks formed along the x axis in the case that polishing streaks are present on a metal film formation surface of a dielectric prism, as illustrated in FIG. 9. FIG. 9 is a diagram that illustrates a state in which a measuring light beam is caused to be totally reflected beneath the metal film formation surface (within the dielectric prism), as observed from above the metal film formation surface (outside the dielectric prism). In the example illustrated in FIG. 9, there are polishing streaks formed along the y axis as well, but it can be clearly seen that the measuring light beam is leaking through polishing streaks formed along the x axis. This is considered to be due to the measuring light beam L not satisfying conditions for total reflection at the metal film formation surface $10a$ at portions where the polishing streaks 52 are present, as illustrated in FIG. 10. As can be understood from FIG. 10, the reason why the measuring light beam L does not satisfy conditions for total reflection at these portions is because the direction (the y axis direction or the direction in which evanescent waves propagate) of the projected components of the measuring light beam L with respect to the metal film formation surface $10a$ is substantially perpendicular to the direction that the polishing streaks 52 extend in (the x axis direction). Accordingly, the sensor chip of the present invention is formed such that projection vectors that represent components of the measuring light beam L with respect to the metal film formation surface $10a$ are substantially parallel to directional vectors that represent the directional properties of the polishing streaks 52. Thereby, the measuring light beam L not satisfying conditions for total reflection at the metal film formation surface $10a$ is prevented, and the problem of leakage of the measuring light beam can be resolved.

As described above, the total reflection illuminated sensor chip C1 of the first embodiment is characterized by the directions of the projected components of the measuring light beam with respect to the metal film formation surface and the direction of the directional properties of the polishing streaks on the metal film formation surface being substantially parallel. Thereby, regions at the interface between the dielectric prism and the metal film, at which the measuring light beam does not satisfy the conditions for total reflection are reduced, resulting in a decrease in the amount of the measuring light beam that leaks through the polishing streaks. Accordingly, autofluorescence of an optical system due to the scattering of the measuring light beam and the influence of fluorescence from floating labels due to scattering of the measuring light beam can be reduced, and more highly quantitative detection becomes possible.

Further, the C1 of the present invention can not only prevent leakage of the measuring light beam through the polishing streaks, but can also prevent the energy of surface plasmon from escaping. For example, in the case that a measuring light beam having a wavelength of 630 nm is irradiated onto an interface between gold (Au) and water, if there is a point at which conditions for total reflection are not satisfied, the energy of surface plasmon accumulated within the gold film escapes from a region having a radius of 3 μm, corresponding to the plasmon propagation length, about the point ("Surface Plasmon Resonance Sensors: Review", J. Homola et al., Sensors and Actuators B: Chemical, Vol. 54, No. 1-2, pp. 3-15, 1999). Further, in the case that the wavelength of the measuring light beam is 850 nm, the radius becomes 24 μm. That is, the energy of surface plasmon accumulated in a region greater than the region at which the conditions for total reflection are not satisfied escapes. Thereby, the electric field enhancing effect of surface plasmon is also greatly reduced. The total reflection illuminated sensor chip C1 of the present invention can prevent the energy of surface plasmon from escaping. Therefore, the electric field enhancing effect of surface plasmon can be efficiently utilized. As a result, signal light (fluorescence emitted by labels and the like) can be efficiently detected, and more highly sensitive measurements can be performed.

<Second Embodiment>

Figure 11A:
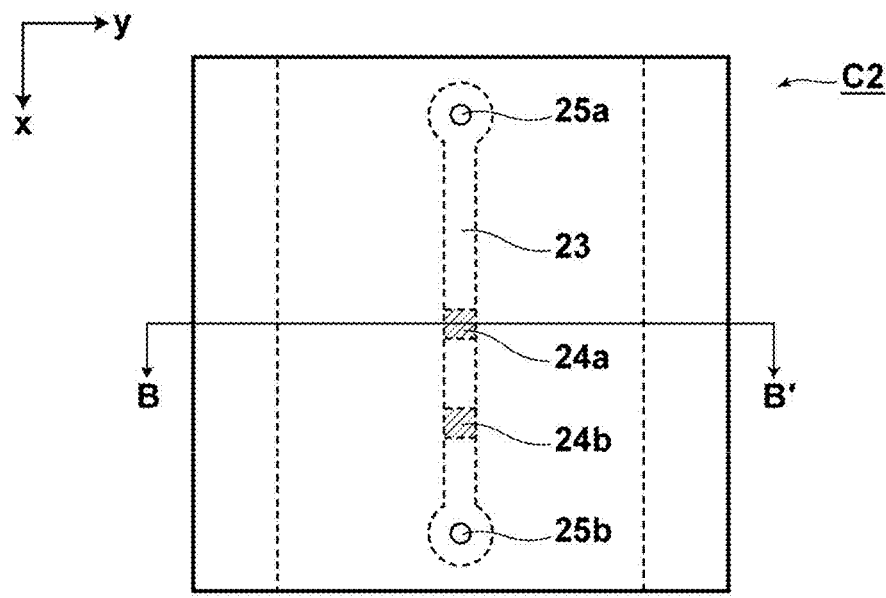
FIG. 11A is a plan view that illustrates the schematic structure of a total reflection illuminated sensor chip according to a second embodiment of the present invention.
Figure 11B:
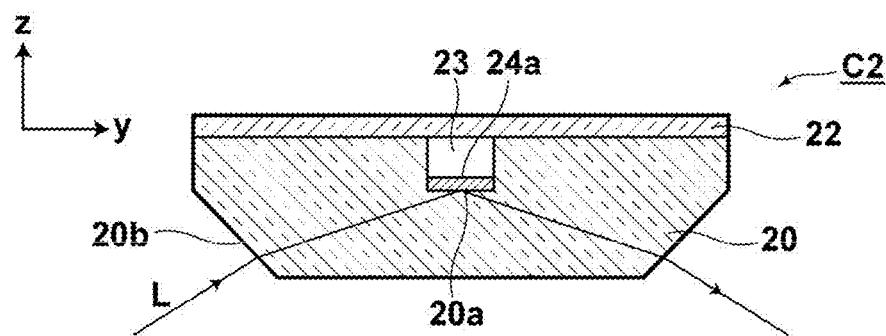
FIG. 11B is a sectional view that illustrates the schematic structure of the total reflection illuminated sensor chip according to the second embodiment of the present invention.

Next, the structure of a total reflection illuminated sensor chip C2 according to a second embodiment of the present invention will be described. FIGS. 11A and 11B are a plan view and a sectional view that illustrates the schematic structure of the total reflection illuminated sensor chip C2 of the second embodiment, respectively. Here, FIG. 11B is a sectional view taken along line B-B' of FIG. 11A. The construction of the total reflection illuminated sensor chip C2 is similar to that of the total reflection illuminated sensor chip C1. However, the total reflection illuminated sensor chip C2 differs from the total reflection illuminated sensor chip C1 in that a flow channel (excluding the top surface thereof) is directly formed in a dielectric prism 20 by molding using a die. Descriptions of elements of the total reflection illuminated sensor chip C2 which are the same as those of total reflection illuminated sensor chip C1 will be omitted insofar as they are not particularly necessary.

As illustrated in FIGS. 11A and 11B, the total reflection illuminated sensor chip C2 is equipped with: the dielectric prism 20; a flow channel 23 (groove) formed in the dielectric prism 20; a lid member 22 that functions as the top surface of the flow channel 23; and metal films 24a and 24b, which are formed at predetermined regions within the flow channel 23.

Figure 12A:
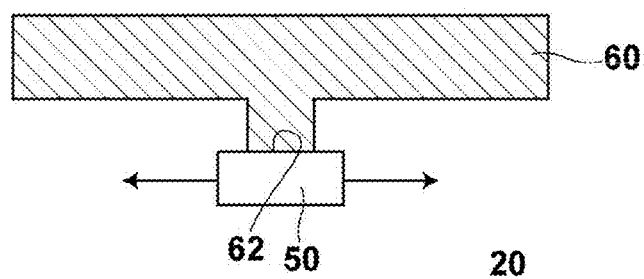
FIGS. 12A through 12D are diagrams that illustrate a method for producing the total reflection illuminated sensor chip according to the second embodiment of the present invention.
Figure 12B:
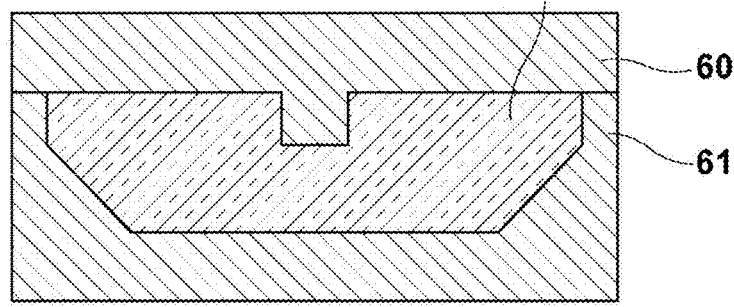
Figure 12C:
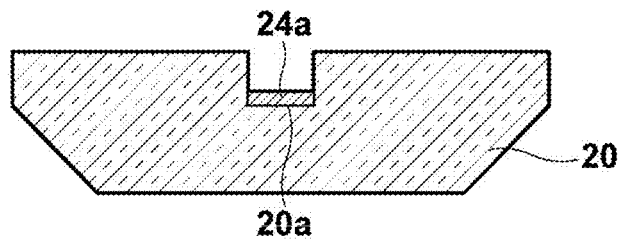
Figure 12D:
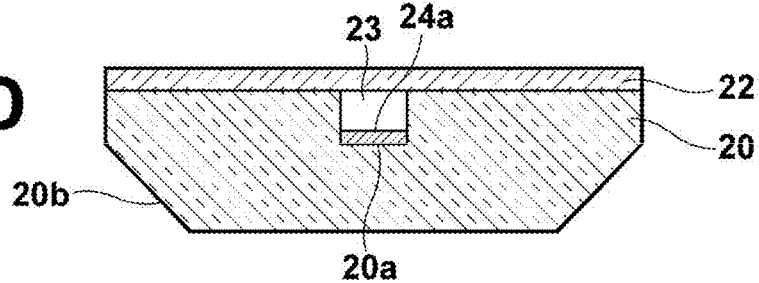

Next, a method for producing the total reflection illuminated sensor chip C2 will be described with reference to FIGS. 12A through 12D. First, a molding die 60 is prepared, and a portion 62 thereof that corresponds to a metal film formation surface 20a (the bottom surface of the flow channel) of the dielectric prism 20 is polished with a polishing material 50 in the directions indicated by the arrows in FIG. 12A, such that polishing streaks are formed along the y axis (FIG. 12A). Next, the die 60 is employed to mold the dielectric prism 20 that functions as the substrate for the sensor chip (FIG. 12B). Thereafter, the metal films 24a and 24b are formed at predetermined regions within the flow channel (FIG. 12C). Finally, the lid member 22 is fitted on dielectric prism (FIG. 12D).

The molding die 60 is a hardened metal die, formed by die steel such as SKD-11 and SKD-61 as defined by JIS (Japanese Industrial Standards). Examples of such die steels include: DC11 by Daido Steel K. K.; SLD by Hitachi Metals K.K.; and KD11 by Nippon Koshuha Steel Co., Ltd.

The polishing of the die 60 is performed such that polishing streaks are formed along the y axis, that is, such that the polishing streaks have directional properties with respect to the direction of the y axis. Specifically, polishing of the die 60 is initially performed by planar milling using a milling tool, or by milling using a planer. Then, finishing is performed, and then lapping is performed manually. The term "finishing" refers to a process in which: a whetstone having a fine abrasive grain is pressed against the surface of a processing target at low pressure; fine parallel vibrations (oscillations) are imparted onto the surface of the processing target; and the processing target is moved perpendicular to the polishing direction, while a large amount of a coolant oil having superior cleansing properties is poured onto the surface of the processing target. The finishing process performs fine cutting to obtain a smooth surface having high accuracy. For example, in the case that a whetstone having a size of 15 mm×15 mm, a pressure of 0.25 Mpa, a whetstone oscillating frequency of 30 Hz, a whetstone oscillating amplitude (twice the oscillating width) of 2 mm, and a processing target conveying speed of 28 m/min are employed to perform finishing for 30 seconds, the polished surface can be finished to have unevenness of 1 µm or less. Lapping is performed by causing a lapping material (a fine grained file) to contact the surface to be processed, and polishing such that the polishing streaks have directional properties with respect to a single direction. Here, the single direction is selected such that the polishing streaks of the dielectric prism, formed by the polishing streaks of the die 60 being transferred thereon, are formed along the y axis. It is preferable for lapping materials having coarse grains (300 grain) to be employed first, then increasing the grain of the lapping material to a fine grain (up to 1000 grain).

In the total reflection illuminated sensor chip C2 of the second embodiment, the direction perpendicular to the flow channel 23 becomes the y axis. Therefore, the portion that corresponds to the bottom surface 20a of the flow channel 23 is polished such that the polishing streaks which will be transferred onto the bottom surface 20a will be perpendicular to the flow channel 23. As in the first embodiment, the polishing may be performed initially in a circular manner such that the entirety of surface is uniformly polished, and then polishing may be performed such that the polishing streaks to be transferred onto the bottom surface of the flow channel ultimately become perpendicular to the flow channel.

The polishing streaks of the total reflection illuminated sensor chip C2 according to the second embodiment differ from the polishing streaks of the total reflection illuminated sensor chip C1 according to the first embodiment in that they are polishing streaks which are transferred from the molding die. That is, the polishing streaks of the total reflection illuminated sensor chip C1 are portions of the dielectric prism 10 which are polished away (elongate grooves), whereas the polishing streaks of the total reflection illuminated sensor chip C2 are portions that protrude from the dielectric prism 20 (elongate ridges). However, even if the polishing streaks are of a structure such as those of the total reflection illuminated sensor chip C2, it can be argued that the same problem of measuring light beams leaking occur. That is, in the total reflection illuminated sensor chip C2 as well, leakage of measuring light beams through the polishing streaks can be prevented, because the polishing streaks have directional properties in the direction of the y axis. In addition, the spatial frequency analysis method described in the first embodiment may be applied to the polishing streaks of the total reflection illuminated sensor chip C2, to define the degree of the directional properties thereof.

As described above, the total reflection illuminated sensor chip C2 of the second embodiment is characterized by the portion of the molding die that corresponds to the metal film formation surface, on which the metal films are formed, being polished such that the polishing streaks have directional properties with respect to a single direction, such that the directions of the projected components of the measuring light beam with respect to the metal film formation surface and the direction of the directional properties of the polishing streaks on the metal film formation surface are substantially parallel. Thereby, regions at the interface between the dielectric prism and the metal film, at which the measuring light beam does not satisfy the conditions for total reflection are reduced, and the energy of surface plasmon can be utilized efficiently. The total reflection illuminated sensor chip C2 of the second embodiment enables obtainment of the same advantageous effects as those obtained by the first embodiment.

<Sensing Apparatus and Sensing Method>

Figure 13:
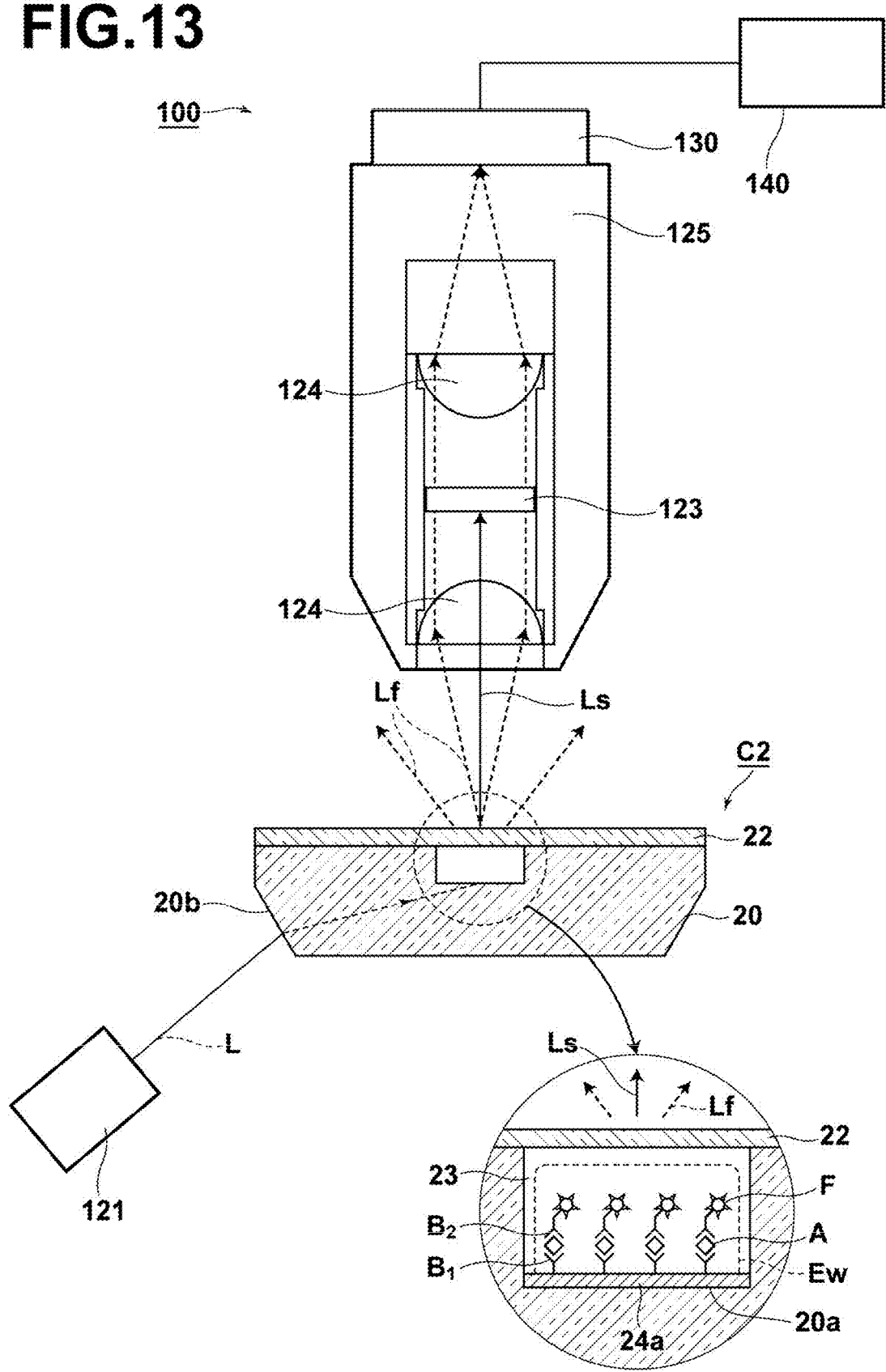
FIG. 13 is a diagram that illustrates the schematic construction of a fluorescence detecting apparatus that employs the sensor chip of the second embodiment.

FIG. 13 is a diagram that illustrates the schematic structure of a fluorescence detecting apparatus that employs the sensor chip C2 of the second embodiment. Note that the detecting apparatus that employ the sensor chip of the present invention is not limited to the fluorescence detecting apparatus illustrated in FIG. 13.

As illustrated in FIG. 13, the fluorescence detecting apparatus is equipped with: the sensor chip C2 of the second embodiment; a light source 121 that emits a measuring light beam L having a wavelength of 657 nm that excites fluorescent labels F; a photodetector 130 for detecting fluorescence Lf emitted by the fluorescent labels F which are supplied onto the sensor chip C2; two planoconvex lenses 124 which are arranged so as to guide the fluorescence Lf to the photodetector 130; an optical filter 123 provided between the two planoconvex lenses 124, for cutting off scattered light Ls of an electric field enhancing field Ew while transmitting the fluorescence Lf; and a data processing section 140 which is connected to the photodetector 130. Here, the light source 121 is provided beneath the sensor chip C2, such that the electric field enhancing field Ew is generated on the sensor chip C2. The fluorescent labels F are immobilized onto the metal film 14a via primary antibodies B1, antigens A and secondary antibodies B2. In addition, reference numeral 125 in FIG. 8 denotes an optical system holding portion, in which the two planoconvex lenses 124 and the optical filter 123 are contained, and to which the photodetector 130 is mounted.

The light source 121 is not particularly limited, and may be a laser light source. The type of light source to be employed as the light source 121 may be appropriately selected according to detection conditions. As described previously, the light source 121 is arranged such that the measuring light beam L output thereby enters the interface between the dielectric prism and the metal film of the sensor chip C2 at a resonance angle that causes total reflection at the interface, and such that surface plasmon resonance occurs at the metal film. Further, a light guiding member may be provided between the light source 121 and the sensor chip total reflection illuminated sensor chip C1 as necessary. In the present invention, the measuring light beam L is irradiated toward the interface between the dielectric prism 20 and the metal film 24a such that projection vectors that represent components of the measuring light beam L, which are projected onto the metal film formation surface 20a, are substantially parallel to directional vectors that represent the directional properties of the polishing streaks. Note that it is preferable for the measuring light beam L to enter the interface in a P polarized state, such that surface plasmon can be induced.

The photodetector 130 is not limited, as long as it is capable of quantitatively detecting the fluorescence Lf emitted by the fluorescent labels F included in a sample S. The photodetector 130 may be selected appropriately according to detection conditions. Examples of photodetectors to be employed as the photodetector 130 include: CCD's, PD's (photodiodes); photomultipliers; and c-MOS's. In addition, the photodetector may be employed in combination with light dividing means, such as an optical filter or a spectroscope, according to detection conditions. Here, the optical filter 123 that cuts off the scattered light Ls and transmits the fluorescence Lf is provided between the two planoconvex lenses 124. Thereby, the fluorescence Lf can be efficiently detected while suppressing noise. That is, the fluorescence Lf can separated from the scattered light Ls and detected. Note that LAS-1000 manufactured by FUJIFILM Corporation is an example of an apparatus equipped with the optical system holding section 125, the two planoconvex lenses 124, the optical filter 123 and the photodetector 130, and can be favorably employed.

The data processing section 140 functions to process fluorescent signal data detected by the photodetector 130. A personal computer is an example of the data processing section 140. Note that the data processing section 140 is not limited to being a personal computer, and may be any electronic calculator or the like, as long as it serves the functions of the data processing section 140.

Figure 14:
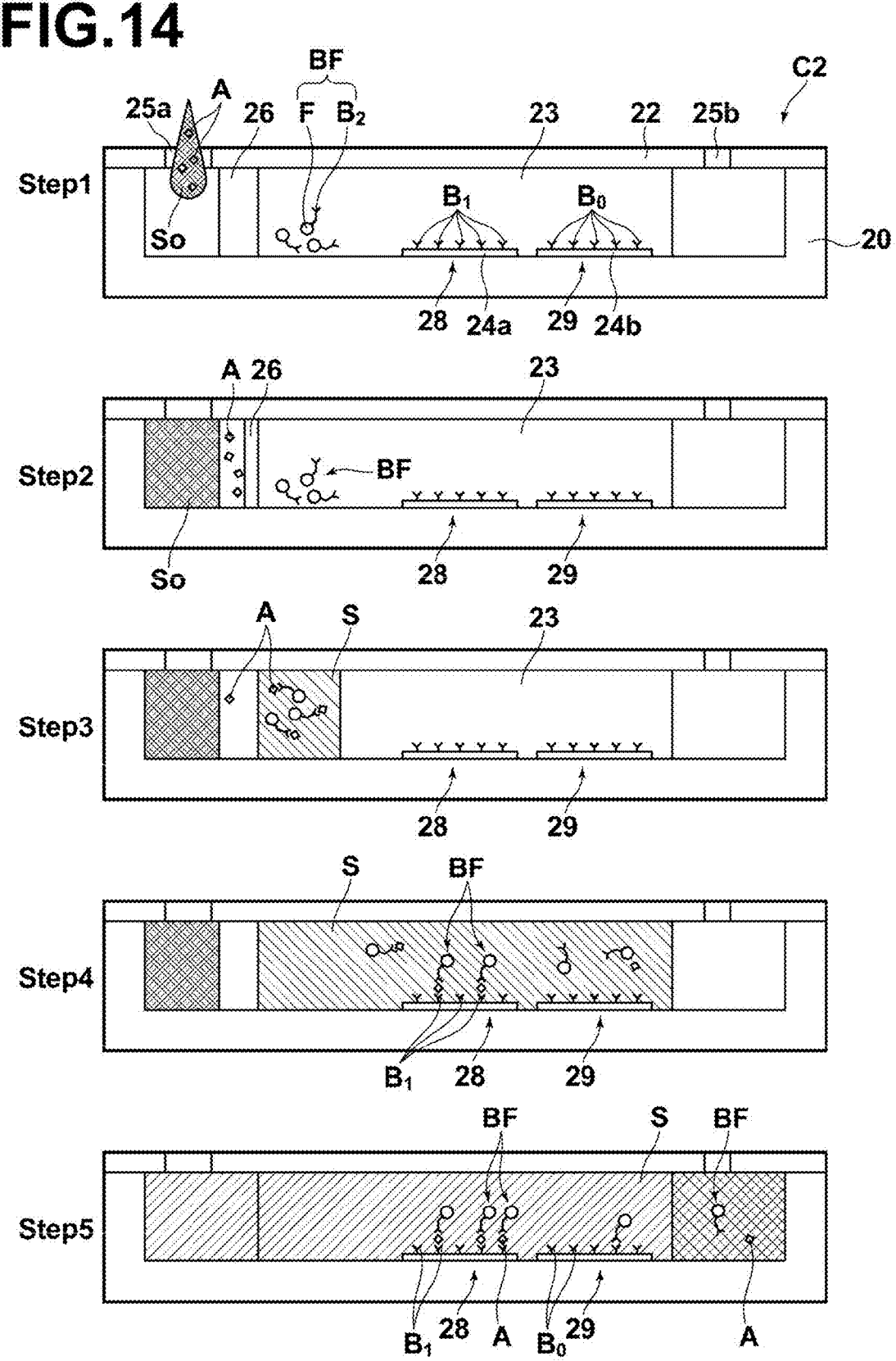
FIG. 14 is a collection of sectional diagrams that illustrates the steps of an assay performed by the sandwich method.

Hereinafter, a fluorescence detecting method of the present invention will be described with reference to FIG. 14 for a case in which the fluorescence detecting apparatus described above is employed to detect antigens A from within a sample S that includes the antigens A.

A case will be considered in which antigens A are detected from within a sample S that includes the antigens A as a detection target substance.

The fluorescence detecting method employed here performs an assay by the sandwich method to be described later. The fluorescent labels F are immobilized onto the metal film 14a via the primary antibodies B1, the antigens A and the secondary antibodies B2. The measuring light beam L emitted by the light source 121 is caused to enter the interface between the dielectric prism and the metal film of the sensor chip C2 at a specific incident angle greater than or equal to a total reflection angle, and such that projection vectors that represent components of the measuring light beam L, which are projected onto the metal film formation surface 20a, are substantially parallel to directional vectors that represent the directional properties of the polishing streaks, to excite evanescent waves Ew. The evanescent waves Ew are caused to resonate with free electrons within the metal film 24a, to generate surface plasmon in the metal film 24a. The fluorescent labels F are excited by the enhancing electric field Ew formed due to the surface plasmon, to generate the fluorescence Lf. The fluorescence Lf is detected by the photodetector 130, and the fluorescent intensity is processed by the data processing section 140.

In the case described above, the presence of the fluorescent labels F is actually directly confirmed by the detection of fluorescence. However, it is considered that the fluorescent labels F would not be immobilized onto the metal film 14a unless the antigens A are present. Therefore, the presence of the antigens A, is indirectly confirmed by confirming the presence of the fluorescent labels F.

The primary antibodies B1 are not particularly limited, and may be appropriately selected according to detection conditions (particularly according to the targets of detection). For example, in the case that the antigens are CRP antigens (molecular weight: 110,000 Da), monoclonal antibodies (having different epitopes from the secondary antibodies B2 at least) that specifically bind with the antigens 2 may be employed as the primary antibodies B1. Known techniques may be employed to immobilize the primary antibodies B1 onto the metal film 14a.

The fluorescent labels F are not particularly limited, as long as they emit the fluorescence Lf of a predetermined wavelength when excited by the measuring light beam L. The fluorescent labels F may be selected appropriately according to measurement conditions (such as the detection target substance and the wavelength of the excitation light beam). In the case that the wavelength of the measuring light beam L is approximately 650 nm, Cy5 pigment (fluorescence: 680 nm, fluorescence quantum yield: 0.3) may be employed, for example.

The enhancing electric field Ew is an electric field which is formed by surface plasmon generated within the metal film 14a. The enhancing electric field Ew is amplified to a greater degree than evanescent waves which are generated at local regions on the metal film 24a. The enhancing electric field Ew amplifies signals, such as fluorescence emitted from the fluorescent labels. Surface plasmon is generated within the metal film 24a by evanescent waves and free electrons within the metal film 24a being caused to resonate.

The assay performed according to the sandwich method that immobilizes the fluorescent labels F onto the metal film 24a is performed by the following steps. The procedures by which an assay is performed according to the sandwich method to detect whether an antigen to be detected is included in blood (whole blood) will be described with reference to FIG. 14.

Step 1: The blood So (whole blood), which is the target of inspection, is injected through the injection opening 25a. Here, a case will be described in which the blood So includes the antigen A to be detected. In FIG. 14, the blood So is represented by the cross hatched regions.

Step 2: The blood So is filtered by a membrane filter 26, and large molecules, such as red blood cells and white blood cells, are separated as residue. Thereafter, plasma S (the blood from which blood cells have been filtered out by the membrane filter 26) leaks out into the flow channel 23 by capillary action. Alternatively, in order to expedite reactions and to shorten detection time, a pump may be connected to the air aperture 25b, and the plasma S may be caused to flow by suctioning and extruding operations of the pump. In FIG. 14, the plasma S is represented by the hatched regions.

Step 3: The plasma S that leaks into the flow channel 23 and labeling secondary antibodies BF, which have been provided upstream of the detecting portion within the flow channel in a dry state, are mixed, and the antigens A within the plasma S bind with the labeling secondary antibodies BF.

Step 4: The plasma S gradually flows along the flow channel 23 toward the air aperture 25b, and the antigens A which are bound to the labeling secondary antibodies BF bind with the primary antibodies B1 which are immobilized onto a measurement sensor portion 28, to form sandwich configurations, in which the antigens A are sandwiched between the primary antibodies B1 and the labeling secondary antibodies BF.

Step 5: A portion of the labeling secondary antibodies BF that did not bind with the antigens A bind with the primary antibodies B1 which are immobilized onto a reference detecting portion 29. Further, even in the case that the labeling secondary antibodies BF which did not bind with the antigens A or the primary antibodies B0 remain, the following plasma S functions as a cleansing agent that washes the labeling secondary antibodies BF, which are floating above the detecting portions, away.

In this manner, the blood So is injected through the injection opening 15a, and step 1 through step 5 are performed to cause the antigens to bind with the primary antibodies and the secondary antibodies. Thereafter, fluorescent signals are detected at the measurement detecting portion 28, to detect the presence and/or the concentration of the antigens at high sensitivity. Next, the sensor chip C2 is moved so as to enable fluorescent signal detection at the reference detecting portion 29, and fluorescent signals are detected at the reference detecting portion 29. The fluorescent signals obtained at the reference detecting portion 29, at which the primary antibodies B0 that bind with the labeling secondary antibodies BF are immobilized, are considered to be fluorescent signals that reflect reaction conditions such as the amount of the labeling secondary antibodies BF which has flowed through the flow channel 23 and the activity thereof. Therefore, if the fluorescent signals obtained at the reference detecting portion 29 are used as a reference to correct the fluorescent signals obtained at the measurement detecting portion 28, more accurate detection results can be obtained. In addition, a known amount of the labeling substance (fluorescent substance or fine metallic particles) may be immobilized onto the reference detecting portion 29 in advance, and the fluorescent signals obtained at the reference detecting portion 29 may be used as a reference to correct the fluorescent signals obtained at the measurement detecting portion.

In the case of the aforementioned homogeneous assay, detection is performed without executing step 5. In addition, an end point method, in which measurement is performed after antigen/antibody reactions are completed has been described. However, the fluorescence detecting method may be a rate method, in which measurements are performed at constant temporal intervals while reactions are occurring (during step 4), to measure variations in the fluorescent signals.

As described above, the fluorescence detecting apparatus and the fluorescence detecting method described above employ the total reflection illuminated sensor chip C2 of the present invention as the sensor chip. Accordingly, regions at the interface between the dielectric prism and the metal film, at which the measuring light beam does not satisfy the conditions for total reflection are reduced, and the energy of surface plasmon can be utilized efficiently, to enable highly sensitive measurements.

EXPERIMENTS (Embodiment)

Figure 15A:
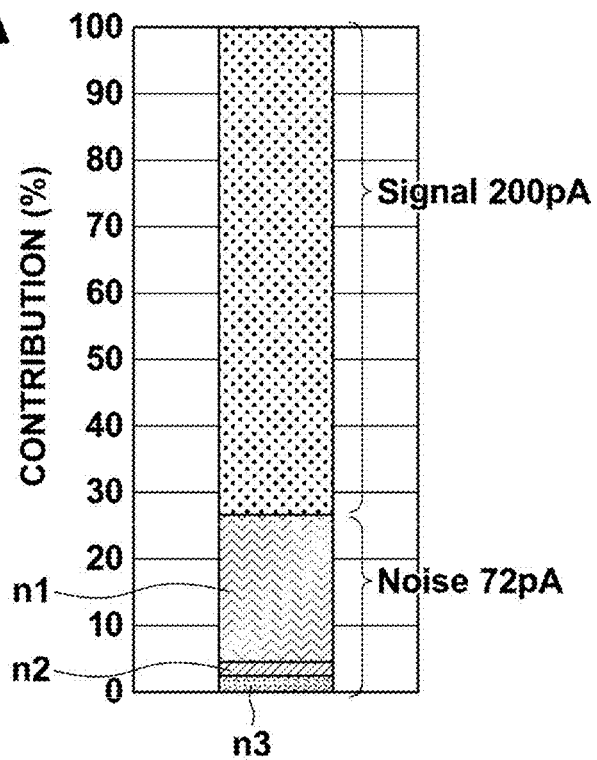
FIG. 15A is a graph that illustrates the ratio between signal light and noise within an entire detected signal obtained using an embodiment of the present invention.

The total reflection illuminated sensor chip C2 of the second embodiment (dielectric prism: PMMA; metal film: vapor deposited Au; thickness of metal film: 50 nm; polishing streaks: directional properties in the y axis direction as illustrated in FIG. 4A) was employed to perform sensing measurements using the fluorescence detecting apparatus illustrated in FIG. 13, with hCG as an antigen (antigen concentration: 90 µM) and anti hCG as an antibody, in which cleansing was performed with PBS after secondary reactions. As a result, a ratio between signal light and noise within an entire detected signal as illustrated in FIG. 15A was obtained.

Comparative Example

A sensor chip having the same features as the total reflection illuminated sensor chip C2, except that polishing streaks had directional properties in the x axis direction as illustrated in FIG. 4B, was employed to perform the same sensing measurement as that performed using the total reflection illuminated sensor chip C2. As a result, a ratio between signal light and noise within an entire detected signal as illustrated in FIG. 15B was obtained.

(Evaluation)

Figure 15B:
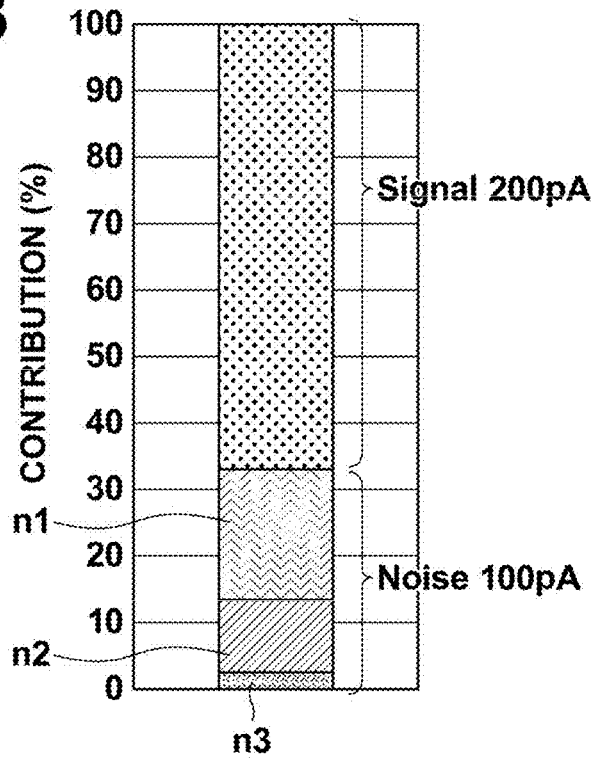
FIG. 15B is a graph that illustrates the ratio between signal light and noise within an entire detected signal obtained using a comparative example.

Within the Noise illustrated in FIGS. 15A and 15B, n1 represents noise due to non specific adsorption of labels, n2 represents noise due to autofluorescence of the apparatus or the optical system, and n3 represents electronic noise that occurs in electronic devices. It was proven that the embodiment of the present invention is capable of reducing n2. In addition, noise constitutes approximately 26% of the entire detected signal in the case that embodiment was employed, whereas noise constitutes approximately 33% of the entire detected signal in the case that the comparative example was employed. Therefore, it can be understood that noise is reduced by employing the total reflection illuminated sensor chip C2 of the present invention. The S/N ratio of the embodiment was 2.8, and the S/N ratio of the comparative example was 2.0. This indicates that the embodiment is capable of measurements up to 1 pM and the comparative example is capable of measurements up to 1.5 pM in the case that the detection limit of a measuring system is (S/N ratio>0.03). Accordingly, it was proven that the embodiment improved the detection limit improved by 1.5 times. In cases that cleansing with PBS was not performed in measurements employing the embodiment and the comparative example, leaked measuring light beams excite floating labels which are not parts of sandwich formations. Therefore, the difference in S/N ratios became greater. Specifically, the embodiment improved the detection limit by 2 times in the case that cleansing was not performed.

What is claimed is:

1. A total reflection illuminated sensor chip, which is employed in a detecting method for detecting a detection target substance including the steps of supplying a liquid sample that includes the detection target substance onto a metal film formed on a surface of a dielectric prism, irradiating a measuring light beam onto the interface between the dielectric prism and the metal film such that conditions for total reflection are satisfied at the interface, and utilizing evanescent waves which are generated due to the irradiation of the measuring light beam to detect the detection target substance, the total reflection illuminated sensor chip comprising:

the dielectric prism, which is formed by a synthetic resin material;

the metal film; and a lid member or a side wall material, which forms a flow channel on the dielectric prism such that the metal film is included within the flow channel, wherein polishing streaks in the region of a metal film formation surface of the dielectric prism, on which the metal film is formed, have directional properties with respect to a single direction; and wherein projection vectors that represent components of the measuring light beam, which are projected onto the metal film formation surface, are substantially parallel to directional vectors that represent the directional properties of the polishing streaks.

2. A total reflection illuminated sensor chip as defined in claim 1, wherein:

the irradiation of the measuring light beam onto the interface between the dielectric prism and the metal film results in evanescent waves and resonance of the metal film, and a direction in which surface plasmon, which is generated by the evanescent waves and resonance of the metal film, propagates is substantially parallel to directional vectors that represent the directional properties of the polishing streaks.

3. A total reflection illuminated sensor chip as defined in claim 1, wherein:

the degree of the directional properties of the polishing streaks is +10% or greater, as calculated by a spatial frequency analysis method.

4. A total reflection illuminated sensor chip as defined in claim 1, wherein the single direction is perpendicular to a length direction of the flow channel.

5. A total reflection illuminated sensor chip as defined in claim 1, is a sensor chip for homogenous assay.

6. A sensing method for detecting a detection target substance, comprising the steps of:

supplying a liquid sample that includes the detection target substance onto a metal film formed on a surface of a dielectric prism, which is formed by a synthetic resin material;

irradiating a measuring light beam onto the interface between the dielectric prism and the metal film such that conditions for total reflection are satisfied at the interface; and utilizing evanescent waves which are generated due to the irradiation of the measuring light beam to detect the detection target substance;

wherein polishing streaks in the region of a metal film formation surface of the dielectric prism, on which the metal film is formed, having directional properties with respect to a single direction; and wherein the measuring light beam is irradiated onto the interface such that projection vectors that represent components of the measuring light beam, which are projected onto the metal film formation surface, are substantially parallel to directional vectors that represent the directional properties of the polishing streaks: and wherein projection vectors that represent components of the measuring light beam, which are projected onto the metal film formation surface, are substantially parallel to directional vectors that represent the directional properties of the polishing streaks.

* * * * *